US012759873B2

(12) United States Patent
Oelmann et al.

(10) Patent No.: US 12,759,873 B2
(45) Date of Patent: Oct. 13, 2026

(54) PROCESS AND PLANT FOR PROVIDING SYNTHESIS GAS AND FOR PRODUCING METHANOL

(71) Applicant: L'Air Liquide, Société Anonyme pour l'Etude et l'Exploitation des Procédés Georges Claude, Paris (FR)

(72) Inventors: Tobias Oelmann, Bad Vilbel (DE); Veronika Gronemann, Karben (DE); Bryce Williams, Frankfurt am Main (DE)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 647 days.

(21) Appl. No.: 18/234,114

(22) Filed: Aug. 15, 2023

(65) Prior Publication Data

US 2024/0059561 A1 Feb. 22, 2024

(30) Foreign Application Priority Data

Aug. 16, 2022 (EP) .................................... 22190457

(51) Int. Cl.
*C01B 3/36* (2026.01)
*C01B 3/50* (2026.01)
(Continued)

(52) U.S. Cl.
CPC .................. *C01B 3/36* (2013.01); *C01B 3/50* (2013.01); *C07C 29/1518* (2013.01);
(Continued)

(58) Field of Classification Search
None
See application file for complete search history.

(56) References Cited

U.S. PATENT DOCUMENTS 5,998,489 A 12/1999 Kobayashi et al.
11,663,804 B2 * 5/2023 Venkatakrishnan .... G01S 17/89 348/222.1
(Continued)

FOREIGN PATENT DOCUMENTS

| | | |
|---|---|---|
| EP | 3 658 494 | 1/2022 |
| WO | WO 2022 079002 | 4/2022 |
| WO | WO 2022 079010 | 4/2022 |

OTHER PUBLICATIONS

European Search Report for corresponding EP 22190457.6, Jan. 23, 2023.

*Primary Examiner* — John J Figueroa
(74) *Attorney, Agent, or Firm* — Allen E. White; Elwood L. Haynes

(57) ABSTRACT

The present invention specifies a process and a plant for production of a synthesis gas stream which makes it possible to produce the synthesis gas stream with a stoichiometry number suitable for the methanol synthesis or other syntheses. To this end an electrolytically produced hydrogen stream is admixed with a hydrocarbon-containing input gas stream and the resulting hydrogen-containing and hydrocarbon-containing input gas stream is reacted in the presence of oxygen to afford synthesis gas in a reforming step. The process mode according to the invention has the advantage that the electrolytically produced hydrogen stream need not be treated, in particular no oxygen need be removed from the electrolytically produced hydrogen stream. The invention further includes a process and a plant for production of methanol including the process according to the invention and the plant according to the invention for production of the synthesis gas stream.

20 Claims, 4 Drawing Sheets

(51) Int. Cl.
*C07C 29/151* (2006.01)
*C07C 29/152* (2006.01)
*C25B 1/04* (2021.01)

(52) U.S. Cl.
CPC .... *C07C 29/152* (2013.01); *C01B 2203/0211* (2013.01); *C01B 2203/0244* (2013.01); *C01B 2203/1223* (2013.01); *C01B 2203/1241* (2013.01); *C25B 1/04* (2013.01)

(56) References Cited

U.S. PATENT DOCUMENTS

| | | | | |
|---|---|---|---|---|
| 11,667,526 | B2 * | 6/2023 | Ott | C01B 3/501<br>252/373 |
| 2007/0282018 | A1 * | 12/2007 | Jenkins | C01B 3/382<br>518/702 |
| 2008/0289820 | A1 * | 11/2008 | De Francesco | C10G 1/047<br>166/257 |
| 2018/0215618 | A1 * | 8/2018 | Kang | C01B 3/48 |
| 2024/0059637 | A1 * | 2/2024 | Oelmann | C07C 29/152 |
| 2025/0145554 | A1 * | 5/2025 | Oelmann | C01B 3/382 |

* cited by examiner

PROCESS AND PLANT FOR PROVIDING SYNTHESIS GAS AND FOR PRODUCING METHANOL

CROSS REFERENCE TO RELATED APPLICATIONS

This application claims the benefit of priority under 35 U.S.C. § 119 (a) and (b) to European Patent Application No. 22190457.6, filed Aug. 16, 2022, the entire contents of which are incorporated herein by reference.

BACKGROUND

Field of the Invention

The invention relates to a process and a plant for producing synthesis gas. The invention further relates to a process for producing methanol comprising the abovementioned process for producing synthesis gas. The invention further relates to a methanol plant for producing methanol comprising the abovementioned plant for producing synthesis gas.

Prior Art

On a large industrial scale methanol is produced from synthesis gas. Synthesis gas is a mixture of predominantly hydrogen ($H_2$), carbon monoxide (CO) and carbon dioxide ($CO_2$). Carbon monoxide and carbon dioxide are often bracketed together under the term "carbon oxides". Inter alia the following two equilibrium reactions (1) and (2) occur simultaneously over a solid methanol synthesis catalyst.

$$CO_2+3H_2 \rightleftharpoons CH_3OH+H_2O \quad (1)$$

$$CO+2H_2 \rightleftharpoons CH_3OH \quad (2)$$

The composition of the synthesis gas is characterized by the so-called stoichiometry number SN defined as $$SN = \frac{n(H_2) - n(CO_2)}{n(CO) + n(CO_2)}, \text{ with } n \text{ in [mol]}.$$

A synthesis gas composition stoichiometrically balanced for methanol synthesis is characterized by a stoichiometry number SN of 2.0. Values of less than 2.0 indicate a hydrogen deficit while values of greater than 2.0 indicate a hydrogen excess. A synthesis gas having a stoichiometry number of less than 2.0 is also referred to as a substoichiometric synthesis gas.

Synthesis gases having a hydrogen deficit are generally obtained in processes comprising a partial oxidation step. These include partial oxidation (PDX) as such and autothermal reforming (ATR).

The main elements of an ATR reactor are a burner, a combustion chamber and a catalyst bed in a refractory-lined pressure jacket. In an ATR reactor the partial oxidation of a hydrocarbon-containing input stream by substoichiometric amounts of oxygen is followed by a steam reforming of the partially oxidized hydrocarbon-containing input stream over a fixed bed of steam reforming catalyst.

For methane as the hydrocarbon a partial oxidation especially proceeds according to the following reaction equation (3).

$$CH_4+1\tfrac{1}{2}O_2 \rightleftharpoons CO+2H_2O \quad (3)$$

The exothermic partial oxidation thus provides steam and the required heat energy for the endothermic steam reforming reaction which proceeds according to reaction equation (4).

$$CH_4+H_2O \rightleftharpoons 3H_2+CO \quad (4)$$

Due to the high temperature the steam reforming (4) also occurs to a certain extent in the combustion chamber of the reactor without involvement of the catalyst. The steam reforming reaction is accompanied by the water gas shift reaction according to reaction equation (5) which is likewise exothermic.

$$CO+H_2O \rightleftharpoons CO_2+H_2 \quad (5)$$

The gas at the outlet of the ATR reactor is normally in or near to thermodynamic equilibrium in respect of the steam reforming and the water gas shift reaction. The employed hydrocarbon often has steam added to it in an ATR. The precise composition of the synthesis gas at the outlet of the reactor depends on the hydrocarbon-to-steam ratio of the input stream, the process temperature and the process pressure. The temperature of the gas mixture at the outlet of the ATR reactor is typically in the range from 950° C. to 1050° C. The process pressure is typically 30 to 80 bar.

One alternative for producing synthesis gas is partial oxidation as such, also known as PDX. The main elements of a PDX reactor are a burner and a combustion chamber which are arranged in a refractory-lined pressure vessel. A PDX reactor effects partial oxidation of a hydrocarbon-containing input stream due to substoichiometric amounts of oxygen. A certain (uncatalyzed) steam reforming also occurs and the water gas shift reaction accompanies the partial oxidation. The above reaction equations (3) to (5) are thus likewise applicable. The temperature of the gas mixture at the outlet of the reactor is typically in the range from 1250° C. to 1450° C. The process pressure is typically 30 to 100 bar.

As mentioned hereinabove the two above-described processes typically provide a markedly substoichiometric synthesis gas, i.e. a synthesis gas having a stoichiometry number of markedly below 2.0. Such a synthesis gas exhibits a hydrogen deficit in respect of the synthesis of methanol. If such a synthesis gas is directly employed for the production of methanol the hydrogen is thus virtually entirely consumed while a substantial portion of the carbon oxides is unconverted. This inter alia has the result that the content of byproducts (in particular higher alcohols and ketones) is higher than desired and that the yield of methanol is suboptimal.

As a result, an industrial process generally supplies a stream of pure hydrogen to the stream of substoichiometric synthesis gas to increase the stoichiometry number SN of the synthesis gas to at least 1.9, preferably to 2.0 or more.

To this end conventional processes separate a portion of the reformed synthesis gas from the main stream and hydrogen from this substream is generally separated by pressure swing adsorption (PSA). The tail gas generated in the pressure swing adsorption contains hydrocarbons and/or carbon monoxide and may therefore be utilized as fuel gas for the ATR or PDX reactor.

If the hydrogen is instead provided by an electrolyzer it is possible to save a portion of the synthesis gas required for the methanol synthesis, thus improving the $CO_2$ footprint of the plant.

EP 3 658 494 B1 therefore proposes admixing hydrogen from an electrolyzer with a synthesis gas stream from a PDX or ATR reactor. In addition, oxygen from an air separation unit is used as oxidant to operate the burner of the PDX or ATR reactor. The hydrogen provided by an electrolyzer typically contains residual oxygen in amounts of up to 1% by volume or more. This is associated with unavoidable diffusion processes occurring inside an electrolysis cell between the anode space and the cathode space. Inter alia a certain amount of the anodically produced oxygen always diffuses through the membrane or the diaphragm from the anode space into the cathode space, thus contaminating the cathodically produced hydrogen.

Oxygen represents a catalyst poison for methanol catalysts and therefore requires ideally quantitative removal from the cathodically produced hydrogen stream before said stream is admixed with the synthesis gas stream from the PDX or ATR unit. This is effected in a so-called de-ox unit. This comprises a catalytic stage for quantitative conversion of the contaminating oxygen with hydrogen from the hydrogen stream to afford water. The water thus catalytically produced is subsequently bound by adsorption, for example on a molecular sieve. This affords an oxygen- and water-free hydrogen stream.

SUMMARY

It is a general object of the present invention to propose a process and a plant for providing a synthesis gas which at least partially overcomes the disadvantages of the prior art.

It is an object of the present invention to propose a process and a plant for providing a synthesis gas, wherein the provided synthesis gas has a composition such that it is immediately suitable for production of methanol over a methanol synthesis catalyst.

It is an object of the present invention to propose a process and a plant for providing a synthesis gas, wherein the adjustment of the stoichiometry number of the synthesis gas is effected by addition of electrolytically produced hydrogen and wherein the electrolytically produced hydrogen employed therefor need not be subjected to a process for removing oxygen.

It is an object of the present invention to propose a process and a plant for providing a synthesis gas having a stoichiometry number of 1.9 or more, wherein the adjustment of the stoichiometry number is effected by addition of electrolytically produced hydrogen and wherein the electrolytically produced hydrogen employed therefor need not be subjected to a process for removing oxygen.

It is a further object of the present invention to propose a process and a plant for producing methanol which at least partially achieves the abovementioned objects.

The independent claims make a contribution to the at least partial achievement of at least one of the above objects. The dependent claims provide preferred embodiments which contribute to the at least partial achievement of at least one of the objects. Preferred embodiments of constituents of one category according to the invention are, where relevant, likewise preferred for identically named or corresponding constituents of a respective other category according to the invention. The terms "having", "comprising" or "containing" etc. do not preclude the possible presence of further elements, ingredients etc. The indefinite article "a" does not preclude possible the presence of a plurality.

The abovementioned objects are at least partially achieved by a process for producing synthesis gas, in particular synthesis gas for methanol synthesis, comprising the steps of:

(a) providing a hydrocarbon-containing input gas stream;
(b) providing an electrolytically produced hydrogen stream;
(c) supplying at least a portion of the electrolytically produced hydrogen stream to the hydrocarbon-containing input gas stream to obtain a hydrogen-containing input gas stream;
(d) reacting the hydrogen-containing input gas stream in the presence of oxygen as oxidant in a reforming step to afford a synthesis gas stream.

The steps (a) to (d) need not necessarily be performed in the specified sequence.

According to the invention the electrolytically produced hydrogen stream is supplied to the hydrocarbon-containing input gas stream according to step (c) before the reaction of the input gas stream to afford synthesis gas according to step (d). The electrolytically produced hydrogen stream is supplied to the hydrocarbon-containing input gas stream especially upstream of the respective reactor configured for the reforming step. This reactor is in particular a PDX reactor or an ATR reactor. The thus-obtained hydrogen-containing input gas stream is then reacted in the presence of oxygen as oxidant to afford synthesis gas according to step (d).

It is therefore possible according to the invention to use an oxygen-containing electrolytically produced hydrogen stream for the reaction according to step (d).

The reforming step according to step (d) is thus necessarily a reforming step in which oxygen is employed in a substoichiometric amount relative to the employed hydrocarbon. If this were not the case it would not be possible to produce a synthesis gas stream from the hydrogen-containing input gas stream. The employed oxygen is thus completely consumed according to step (d) so that the produced synthesis gas stream is free from oxygen.

If the electrolytically produced hydrogen stream were supplied to the synthesis gas stream only after the reaction according to step (d) as per the prior art this would require a quantitative removal of oxygen from the electrolytically produced hydrogen stream. As described above oxygen represents a catalyst poison for methanol synthesis catalysts and other catalyst types.

The hydrogen-containing input gas stream produced according to step (c) is composed of the hydrocarbon-containing input gas stream and the electrolytically produced hydrogen stream. The "hydrogen-containing input gas stream" is thus a hydrogen-containing and hydrocarbon-containing input gas stream.

The electrolytically produced hydrogen stream is provided by an electrolyzer. Depending on the process mode a portion of the thus electrolytically produced hydrogen stream is supplied to the hydrocarbon-containing input gas stream or the entire thus electrolytically produced hydrogen stream is supplied to the hydrocarbon-containing input gas stream. The electrolyzer is preferably configured such that the entire electrolytically produced hydrogen stream is supplied to the hydrocarbon-containing input gas stream. The electrolyzer may then be operated under full load for most of the time. The electrolyzer is then preferably configured such that the resulting synthesis gas stream produced from the hydrogen-containing input gas stream has a stoichiometry number suitable for methanol synthesis.

The electrolytically produced hydrogen stream may be produced by any electrolysis process familiar to those skilled in the art. The electrolysis process is preferably a water electrolysis. Examples include alkaline electrolysis, proton exchange membrane electrolysis (PEM electrolysis), anion exchange membrane electrolysis (AEM electrolysis), high-temperature electrolysis (HTE) and electrolysis using solid oxide electrolyzer cells (SOEC).

The hydrocarbon-containing input gas stream preferably comprises methane ($CH_4$) as a main component. The hydrocarbon-containing input gas stream preferably comprises at least 50% by volume of methane or at least 75% by volume of methane or at least 90% by volume of methane or at least 95% by volume of methane.

The synthesis gas stream comprises synthesis gas. A synthesis gas is a gas mixture which comprises at least a carbon oxide (carbon monoxide or carbon dioxide) and hydrogen. The synthesis gas preferably comprises carbon monoxide, carbon dioxide and hydrogen.

A reforming step is in principle to be understood as meaning the chemical reaction of hydrocarbons with oxygen and/or steam to afford a synthesis gas.

A preferred embodiment of the process according to the invention is characterized in that the reforming step comprises an autothermal reforming (ATR) or a partial oxidation (PDX) of the hydrogen-containing input gas stream.

A preferred embodiment of the process according to the invention is characterized in that an amount of electrolytically produced hydrogen stream supplied to the hydrocarbon-containing input gas stream according to step (c) is adjusted such that a synthesis gas stream having a stoichiometry number SN of 1.9 to 2.5, preferably of 2.0 to 2.4, is obtained according to step (d), wherein $$SN = \frac{n(H_2) - n(CO_2)}{n(CO) + n(CO_2)}, \text{ with } n \text{ in [mol]}.$$

This ensures that a synthesis gas stream which is directly, i.e. immediately, employable for a downstream methanol synthesis is obtained. The thus-obtained synthesis gas stream can at least be used for a downstream methanol synthesis without any need for a further supply of hydrogen. The thus obtained synthesis gas stream is likewise employable immediately or at least without further supply of hydrogen for other syntheses which require synthesis gas compositions having a corresponding stoichiometry number.

A preferred embodiment of the process according to the invention is characterized in that the electrolytically produced hydrogen stream contains oxygen as an impurity and the oxygen present as an impurity is not removed before the supplying of the electrolytically produced hydrogen stream to the hydrocarbon-containing input gas stream according to step (c).

As elucidated above it is not necessary according to the invention to remove oxygen present as an impurity in the electrolytically produced hydrogen stream by a complex purification process. The oxygen produced as an impurity in the electrolytically produced hydrogen stream is entirely consumed as oxidant in the reforming step (d).

A further preferred embodiment of the process according to the invention is characterized in that the electrolytically produced hydrogen stream contains water and the water is not removed before the supplying of the electrolytically produced hydrogen stream to the hydrocarbon-containing input gas stream according to step (c).

Since the reforming step according to step (d) at least partially also comprises a steam reforming and steam is thus consumed it is also not necessary to dry the electrolytically produced hydrogen stream. Without further workup an electrolytically produced hydrogen stream always contains certain amounts of residual water since the separation in the gas-liquid separator of an electrolyzer or a comparable apparatus is never complete.

The electrolytically produced hydrogen stream may contain up to 5% by volume of oxygen or 0.01% to 5% by volume of oxygen or 0.1% to 3% by volume of oxygen or 0.1% to 1% by volume of oxygen as an impurity.

A preferred embodiment of the process according to the invention is characterized in that the process comprises providing an electrolytically produced oxygen stream, wherein the electrolytically produced oxygen stream is used as oxidant in step (d).

The reforming step according to step (d) in principle proceeds in the presence of oxygen as oxidant. Air or oxygen-enriched air or pure oxygen may be employed here. The oxidant is in particular supplied to the burner of a PDX or ATR unit and the hydrogen-containing and hydrocarbon-containing input gas is therein reacted with a substoichiometric amount of oxygen to afford synthesis gas.

An electrolyzer typically produces oxygen as a "byproduct", wherein this byproduct is often not utilized. The use of the electrolytically produced oxygen as oxidant for the reforming step according to step (d) thus represents an improvement in the process integration of the process according to the invention.

As an alternative the process comprises providing an oxygen stream produced by air separation, wherein the oxygen stream produced by air separation is used as oxidant in step (d).

Alternatively the oxygen may also be provided to the process via a pipeline.

A preferred embodiment of the process according to the invention is characterized in that a steam stream is supplied to the hydrocarbon-containing input gas stream or the hydrogen-containing input gas stream.

A steam stream is optionally supplied to the hydrocarbon-containing input gas stream or the hydrogen-containing input gas stream, especially when the reforming step comprises an autothermal reforming (ATR).

Additional steam is preferably supplied when the reforming step comprises an autothermal reforming. This advantageously prevents carbon deposits on the catalyst utilized for the endothermic steam reforming in the ATR reactor. The term "additional steam" is to be understood as meaning steam which is not reaction-internally produced by the partial oxidation reaction. Depending on whether the supplying of the steam stream is effected before or after the supplying of the electrolytically produced hydrogen stream to the hydrocarbon-containing input gas stream, addition of a steam stream accordingly results in a steam-containing and hydrogen-containing input gas stream. Since it is hydrocarbon-containing the latter can also be referred to as a steam-containing, hydrogen-containing and hydrocarbon-containing input gas stream.

A preferred embodiment of the process according to the invention is characterized in that the hydrocarbon-containing input gas stream is a natural gas stream or a biogas stream.

The natural gas stream or the biogas stream in particular contains methane ($CH_4$) as the primary component. The natural gas stream or biogas stream preferably comprises at least 50% by volume of methane or at least 75% by volume of methane or at least 90% by volume of methane or at least 95% by volume of methane. The biogas stream is preferably a pretreated biogas stream, wherein the pretreatment preferably consists of increasing the concentration of methane and reducing the concentration of undesired concomitants, in particular of carbon dioxide.

The abovementioned objects are further at least partially achieved by a process for producing methanol comprising the process for producing synthesis gas according to any of the abovementioned embodiments, further comprising the step of reacting the synthesis gas stream over a solid methanol synthesis catalyst to afford raw methanol, wherein the raw methanol comprises at least methanol ($CH_3OH$) and water.

The produced synthesis gas stream is preferably converted into raw methanol over a solid methanol synthesis reactor directly, in particular without a further modification step or without further supplying of a hydrogen stream. The synthesis gas of the synthesis gas stream used for the methanol synthesis preferably has a stoichiometry number SN of 1.9 to 2.5, preferably of 2.0 to 2.4.

The synthesis gas of the synthesis gas stream employed for the methanol synthesis and produced according to the invention may also be referred to as synthesis make-up gas. This synthesis gas is in most cases distinguishable in terms of its composition from the synthesis gas which is actually introduced into the respective methanol synthesis reactor. As is known to those skilled in the art the methanol synthesis is on the large industrial scale generally configured as a synthesis loop, i.e. synthesis gas unreacted in the methanol synthesis reactor is recycled to the reactor inlet after separation of condensed-out raw methanol. This recycled synthesis gas, also known as recycle gas, is mixed with the synthesis make-up gas. The resulting mixed synthesis gas of composition as at the reactor inlet may have a stoichiometry number diverging from the abovementioned interval for the synthesis make-up gas.

A preferred embodiment of the process according to the invention for producing methanol is characterized in that the raw methanol is separated into pure methanol and water in a thermal separation process.

The thermal separation process is a process known to those skilled in the art such as distillation or rectification.

A preferred embodiment of the process according to the invention for producing methanol is characterized in that the water separated in the thermal separation process is used as starting material for the electrolytically produced hydrogen.

It is preferable when the water separated in the thermal separation process is worked up and subsequently used as starting material for the electrolytically produced hydrogen. The water separated in the thermal separation process often contains sodium hydroxide (NaOH) which must be removed for the utilization of the water in a PEM electrolysis for example. If the electrolytically produced hydrogen stream is produced by an alkaline electrolysis the removal of sodium hydroxide is not absolutely necessary since the alkaline electrolysis employs highly concentrated aqueous potassium hydroxide solution ($KOH_{aq}$) or aqueous sodium hydroxide solution ($NaOH_{aq}$) as electrolysis medium.

The utilization of the water separated in the thermal separation process as starting material for the electrolytically produced hydrogen improves the process integration since fewer resources are required for the provision of water for the water electrolysis.

The water separated in the thermal separation process may further be used as starting material for electrolytically produced oxygen.

A preferred embodiment of the process according to the invention for producing methanol is characterized in that reacting the synthesis gas stream over the solid methanol synthesis catalyst to afford raw methanol generates a residual gas stream containing synthesis gas unconverted into raw methanol, wherein a portion of the residual gas stream is separated as a purge gas stream and wherein the purge gas stream is supplied to a hydrogen recovery apparatus to produce a non-electrolytically produced hydrogen stream and

- the non-electrolytically produced hydrogen stream is at least partially supplied to the hydrocarbon-containing input gas stream in addition to the electrolytically produced hydrogen stream to obtain the hydrogen-containing input gas stream according to step (c) and/or
- the non-electrolytically produced hydrogen stream is at least partially supplied to the synthesis gas stream obtained according to step (d).

As mentioned hereinabove, on an industrial scale the synthesis of methanol is typically carried out within a so-called synthesis loop. The reaction of the synthesis gas over the methanol synthesis catalyst is incomplete due to the establishment of a thermodynamic equilibrium and not only condensable raw methanol but also a non-condensable residual gas stream containing unconverted synthesis gas are obtained at the outlet of the respective reactor. A portion of this residual gas stream is recycled to the reactor inlet for renewed reaction to afford raw methanol. This recycled stream is referred to as a recycle gas stream. A portion is separated as a purge gas stream to avoid accumulation of compounds inert under the conditions of methanol synthesis in the synthesis loop.

This purge gas stream containing hydrogen from the unconverted synthesis gas (residual gas stream) is advantageously supplied to a hydrogen recovery apparatus in order thus to produce a non-electrolytically produced hydrogen stream.

In one embodiment said stream is supplied to the hydrocarbon-containing input gas stream in addition to the electrolytically produced hydrogen stream to obtain the hydrogen-containing input gas stream.

Alternatively or in addition the non-electrolytically produced hydrogen stream is supplied to the synthesis gas stream downstream of the respective reformer (PDX or ATR) and upstream of the methanol synthesis.

Since a methanol plant having a synthesis loop especially generates a purge gas stream said stream may advantageously be utilized process-internally and the electrolyzer required for producing the electrolytically produced hydrogen stream may accordingly be made smaller.

The hydrogen recovery apparatus may for example be a membrane unit or a pressure swing adsorption apparatus (PSA). A PSA is preferred. In this connection a preferred embodiment of the process according to the invention for producing methanol is characterized in that an amount of electrolytically produced hydrogen stream and of non-electrolytically produced hydrogen stream supplied to the hydrocarbon-containing input gas stream according to step (c) is adjusted such that a synthesis gas stream having a stoichiometry number SN of 1.9 to 2.5, preferably of 2.0 to 2.4, is obtained according to step (d), wherein $$SN = \frac{n(H_2) - n(CO_2)}{n(CO) + n(CO_2)}, \text{ with } n \text{ in [mol]}.$$

In this connection an embodiment of the process according to the invention for producing methanol alternative to the preceding embodiment is characterized in that an amount of electrolytically produced hydrogen stream supplied to the hydrocarbon-containing input gas stream according to step (c) and an amount of non-electrolytically produced hydrogen stream supplied to the synthesis gas stream is adjusted such that a synthesis gas stream having a stoichiometry number SN of 1.9 to 2.5, preferably of 2.0 to 2.4, is obtained, wherein $$SN = \frac{n(H_2) - n(CO_2)}{n(CO) + n(CO_2)}, \text{ with } n \text{ in [mol]}.$$

The abovementioned objects are further at least partially achieved by a plant for producing synthesis gas, wherein the plant comprises the following components in fluid connection with one another:

(a) means configured for providing a hydrocarbon-containing input gas stream;
(b) an electrolyzer configured for providing an electrolytically produced hydrogen stream;
(c) means configured for supplying at least a portion of the electrolytically produced hydrogen stream to the hydrocarbon-containing input gas stream which make it possible to produce a hydrogen-containing input gas stream;
(d) a reactor configured for reacting the hydrogen-containing input gas stream in the presence of oxygen as oxidant in a reforming step which makes it possible to produce a synthesis gas stream.

The plant for producing synthesis gas may alternatively also be referred to as a synthesis gas production plant.

A preferred embodiment of the plant is characterized in that the reactor (d) is an autothermal reformer or a reactor configured for a partial oxidation.

A preferred embodiment of the plant is characterized in that the means (c) are configured such that an amount of electrolytically produced hydrogen stream suppliable to the hydrocarbon-containing input gas stream is adjustable such that a synthesis gas stream having a stoichiometry number SN of 1.9 to 2.5, preferably of 2.0 to 2.4, is producible according to (d), wherein $$SN = \frac{n(H_2) - n(CO_2)}{n(CO) + n(CO_2)}, \text{ with } n \text{ in [mol]}.$$

A preferred embodiment of the plant is characterized in that the plant includes no means for removing oxygen occurring as an impurity from the electrolytically producible hydrogen stream.

A preferred embodiment of the plant is characterized in that the electrolyzer is configured for providing an electrolytically produced oxygen stream and the plant comprises means for using the oxygen stream as oxidant in the reactor (d) for reacting the hydrogen-containing input gas stream to afford the synthesis gas stream.

A preferred embodiment of the plant is characterized in that the plant comprises an apparatus for air separation, wherein the apparatus for air separation makes it possible to produce an oxygen stream and the plant comprises means for using the oxygen stream as oxidant in the reactor for reacting the hydrogen-containing input gas stream to afford the synthesis gas stream.

The oxygen stream may alternatively be provided via a pipeline.

The abovementioned objects are further at least partially achieved by a methanol plant for producing methanol comprising a plant for producing synthesis gas according to any of the abovementioned embodiments, characterized in that the methanol plant comprises a methanol synthesis reactor, wherein the methanol synthesis reactor is configured for reacting the synthesis gas producible by the plant to afford raw methanol, wherein the raw methanol contains at least methanol ($CH_3OH$) and water.

A preferred embodiment of the methanol plant is characterized in that the methanol plant comprises a thermal separation apparatus, wherein the thermal separation apparatus is configured for separating the raw methanol into pure methanol and water.

A preferred embodiment of the methanol plant is characterized in that the methanol plant comprises means for using the separated water as starting material for the electrolytically producible hydrogen.

A preferred embodiment of the methanol plant is characterized in that a residual gas stream is producible through the reacting of the synthesis gas producible by the plant to afford raw methanol, wherein the residual gas stream contains synthesis gas unconverted into raw methanol and the methanol plant comprises means for separating a purge gas stream from the residual gas stream and the methanol plant comprises a hydrogen recovery apparatus and means for supplying the purge gas stream to the hydrogen recovery apparatus, thus making it possible to produce a non-electrolytically produced hydrogen stream from the purge gas stream using the hydrogen recovery apparatus, and the methanol plant comprises

- means for supplying at least a portion of the non-electrolytically produced hydrogen stream to the hydrocarbon-containing input gas stream in addition to the electrolytically produced hydrogen stream, thus making it possible to produce the hydrogen-containing input gas stream according to (c) and/or
- means for supplying at least a portion of the non-electrolytically produced hydrogen stream to the synthesis gas stream producible according to (d).

In this context a preferred embodiment of the methanol plant is characterized in that the means (c) and the means for supplying the non-electrolytically produced hydrogen stream are configured such that an amount of electrolytically produced hydrogen stream and of non-electrolytically produced hydrogen stream suppliable to the hydrocarbon-containing input gas stream is adjustable such that a synthesis gas stream having a stoichiometry number SN of 1.9 to 2.5, preferably of 2.0 to 2.4, is producible according to (d), wherein $$SN = \frac{n(H_2) - n(CO_2)}{n(CO) + n(CO_2)}, \text{ with } n \text{ in [mol]}.$$

In this context an embodiment of the methanol plant alternative to the preceding embodiment is characterized in that the means (c) and the means for supplying at least a portion of the non-electrolytically produced hydrogen stream to the synthesis gas stream producible according to (d) are configured such that a synthesis gas stream having a stoichiometry number SN of 1.9 to 2.5, preferably of 2.0 to 2.4, is producible, wherein $$SN = \frac{n(H_2) - n(CO_2)}{n(CO) + n(CO_2)}, \text{ with } n \text{ in [mol]}.$$

BRIEF DESCRIPTION OF THE DRAWINGS

The invention is more particularly elucidated hereinbelow by way of working examples and numerical examples without in this way limiting the subject-matter of the invention. Further features, advantages and possible applications of the invention will be apparent from the following description of the working examples in connection with the drawings and the numerical examples. In the figures, functionally and/or structurally identical or at least similar constituents are given identical reference numerals.

In the figures.

DETAILED DESCRIPTION OF PREFERRED EMBODIMENTS

Figure 1:
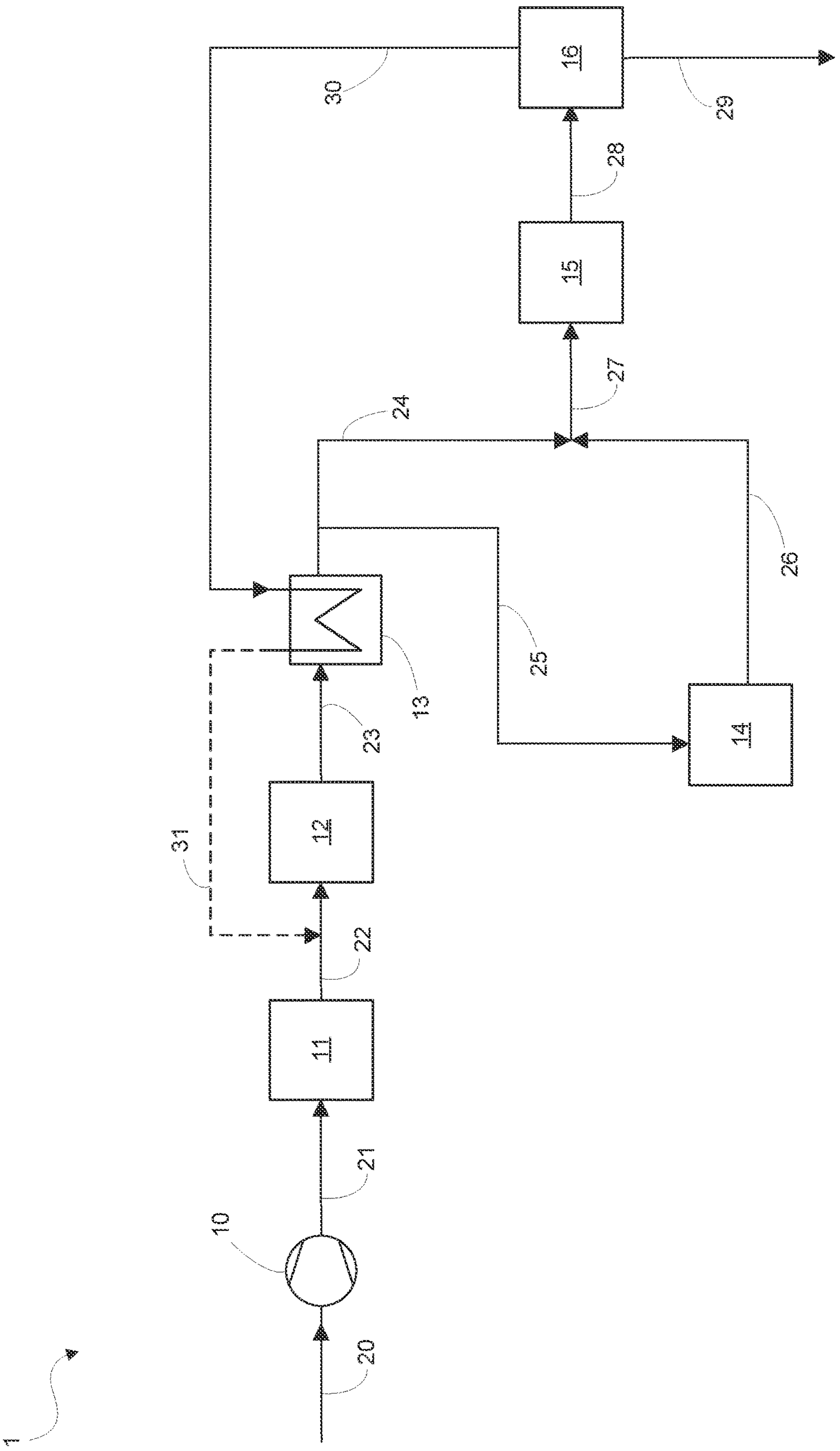
FIG. 1 shows a block flow diagram of a process for synthesis gas production and methanol production according to the prior art using PSA hydrogen.

FIG. 1 shows a highly simplified block flow diagram of an example of a process 1 for synthesis gas production and subsequent methanol production according to conventional processes from the prior art.

A hydrocarbon-containing input gas stream, here a natural gas stream, is supplied via conduit 20 and initially compressed in compressor 10. The compressed input gas is subsequently sent on via conduit 21 and freed of undesired concomitants in a unit for purification of natural gas 11. Purification unit 11 comprises for example a hydrodesulfurization plant for removal of sulfur compounds. The purified input gas is sent on via conduit 22 and mixed with steam supplied via conduit 31. The mixture of input gas and steam is subsequently reacted in an autothermal reformer 12 to afford a synthesis gas stream. The autothermal reformer is supplied with air, oxygen-enriched air or pure oxygen via a conduit (not shown). The synthesis gas produced in the autothermal reformer is sent on via conduit 23 and cooled in a unit for heat recovery 13. The unit for heat recovery 13 simultaneously converts process water from conduit 30 into steam which is sent on via conduit 31 and, as mentioned, combined with the hydrocarbon-containing input gas stream in conduit 22.

The cooled synthesis gas stream exiting the unit for heat recovery 13 has a stoichiometry number of markedly below 2.0 and therefore cannot be immediately employed for a subsequent methanol synthesis. For this reason a substream is removed from the synthesis gas stream of conduit 24 via conduit 25 and sent to a unit for pressure swing adsorption 14. The unit for pressure swing adsorption 14 produces a stream of largely pure hydrogen which is discharged from the pressure swing adsorption unit 14 via conduit 26. The unit for pressure swing adsorption 14 simultaneously produces a tail gas stream (not shown) which may for example be partially employed in the autothermal reformer 12 or else used for under-firing in a separate fired heater.

The hydrogen stream discharged from the unit for pressure swing adsorption 14 via conduit 26 is combined with the synthesis gas stream from conduit 24, thus resulting in a hydrogen-enriched synthesis gas stream which is sent on via conduit 27. The hydrogen-enriched synthesis gas stream in conduit 27 has a stoichiometry number of above 2.0 and may therefore be used for a subsequent methanol synthesis. Accordingly the synthesis gas stream is introduced into a unit for methanol synthesis 15 via conduit 27. The unit for methanol synthesis 15 may comprise one or more serially connected methanol synthesis reactors. In the methanol synthesis reactor(s) the hydrogen and the carbon oxides from the hydrogen-enriched synthesis gas stream are reacted over a solid methanol synthesis catalyst to afford raw methanol, a mixture of methanol and water. The raw methanol is subsequently sent on via conduit 28 and supplied to a distillation unit 16. Distillation unit 16 comprises a rectification column for example. The distillation unit separates the methanol from water and undesired byproducts. A stream of pure methanol is discharged from the distillation unit 29 via conduit 29 in addition to a stream of process water which is discharged via conduit 30. The process water in conduit 30 is converted into steam in the unit for heat recovery 13.

Figure 2:
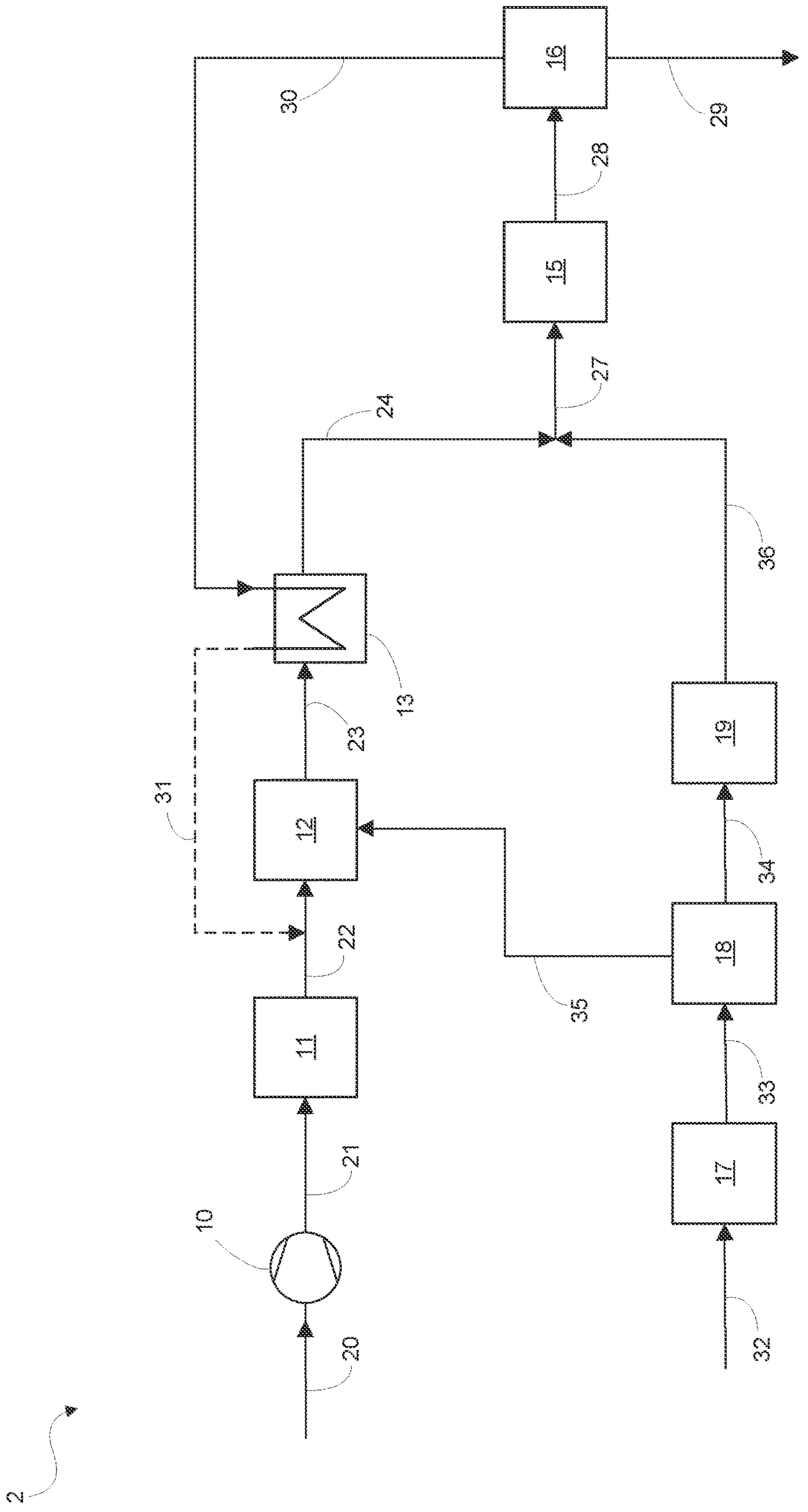
FIG. 2 shows a block flow diagram of a process for synthesis gas production and methanol production according to the prior art using electrolytically produced hydrogen.

FIG. 2 shows a highly simplified block flow diagram of an example of a process 2 for synthesis gas production and subsequent methanol production according to the principle as described in EP 3 658 494 B1.

Compared to process 1 the hydrogen required for adjusting the stoichiometry number of the synthesis gas produced by reforming is produced by an electrolyzer 18. It is accordingly unnecessary to divert a substream from the cooled synthesis gas stream in conduit 24 and produce hydrogen therefrom in a unit for pressure swing adsorption, as described for FIG. 1.

Accordingly, a raw water stream is supplied via conduit 32 and purified, for example desalinized, in a unit for water treatment 7. The resulting pure water stream is sent on via conduit 33 and subjected to a water electrolysis in the electrolyzer 18, thus producing an electrolytically produced hydrogen stream and an electrolytically produced oxygen stream. The electrolysis may for example be a PEM electrolysis or an alkaline electrolysis. An oxygen stream is withdrawn from the electrolyzer 18 via conduit 35 and used in the autothermal reformer 12 and therefore supplied thereto as oxidant. The electrolytically produced hydrogen stream likewise produced in the electrolyzer is sent on via conduit 34. The hydrogen stream in conduit 34 contains oxygen as an impurity, for example 1% by volume, and optionally residual amounts of water not removed in the gas-liquid separator of the electrolyzer 18. The hydrogen stream is therefore supplied to a unit for purifying electrolysis hydrogen 19. In this purification unit 19 the oxygen present as an impurity is initially catalytically reacted with hydrogen of the hydrogen stream to afford water. This catalytically produced water and the abovementioned residual water is subsequently bound by adsorption, for example on a molecular sieve. The electrolytically produced hydrogen stream exiting the purification unit 19 is accordingly free from oxygen and dry, i.e. anhydrous. This purified hydrogen stream is sent on via conduit 36 and combined with the cooled synthesis gas stream from conduit 24. This results in a hydrogen-enriched synthesis gas stream having a stoichiometric number of more than 2.0 and which can therefore be used for the subsequent methanol synthesis in the unit for methanol synthesis 15.

Figure 3:
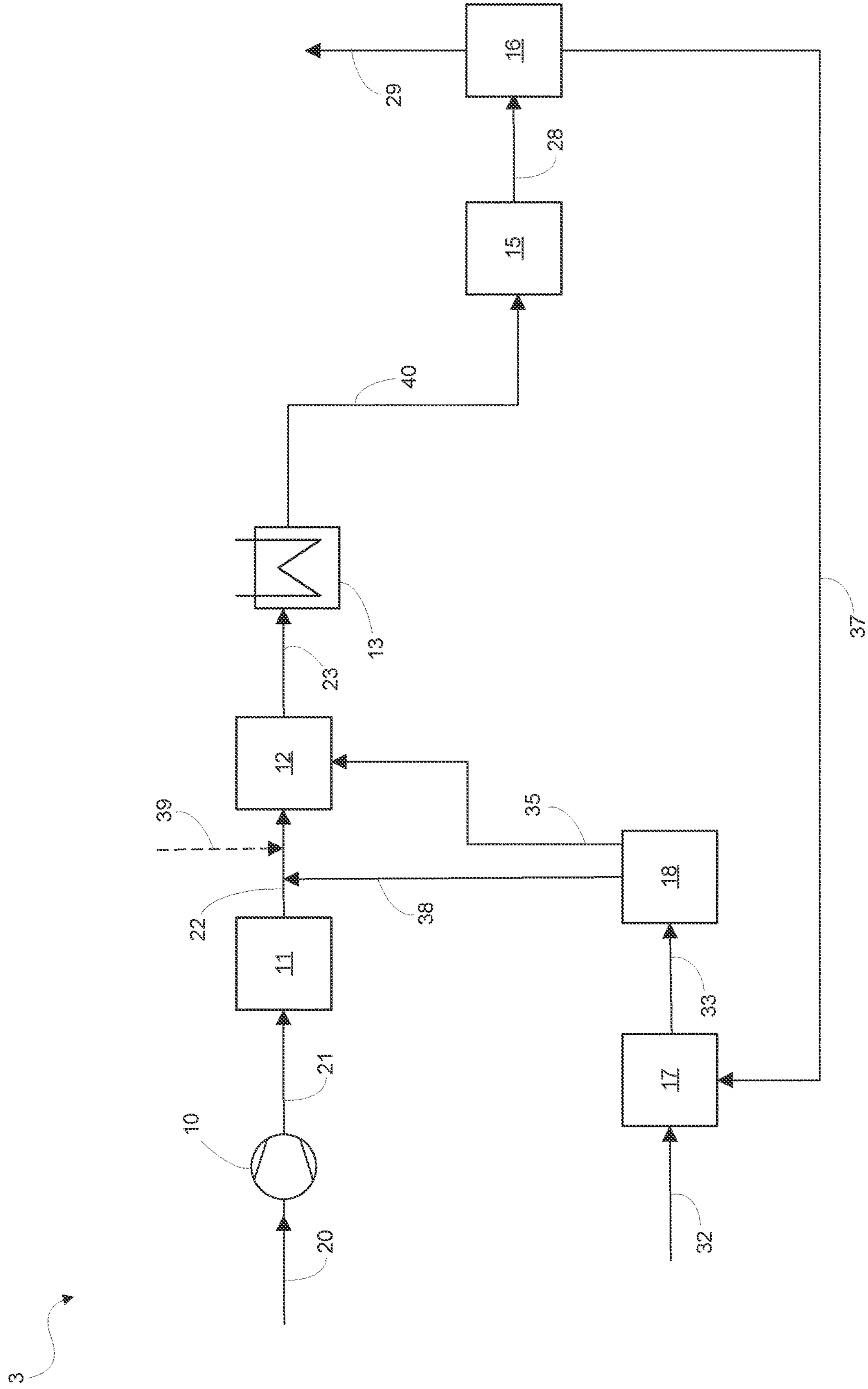
FIG. 3 shows a block flow diagram of a process for synthesis gas production and methanol production according to the invention and FIG. 4 shows a block flow diagram of a further process for synthesis gas production and methanol production according to the invention.

FIG. 3 shows a highly simplified block flow diagram of an example of a process 3 for synthesis gas production and subsequent methanol production according to the invention.

The process mode according to process 3 differs from process 2 especially in that the hydrogen stream electrolytically produced by the electrolyzer 18 is supplied to the purified hydrocarbon-containing input gas stream in conduit 22 via conduit 38. As described in detail for FIG. 1 a hydrocarbon-containing input gas stream, here a natural gas stream, is supplied via conduit 20 according to process 3 too. The hydrocarbon-containing input gas stream is subsequently compressed via compressor 10, sent on via conduit 21 and purified in the unit for purifying the input gas 11. The purification unit 11 includes a hydrodesulfurization plant for removing sulfur compounds from the input gas stream. The purified, hydrocarbon-containing input gas stream is sent on via conduit 22 and as described above combined with the electrolytically produced hydrogen stream from conduit 38. The resulting hydrogen-containing and hydrocarbon-containing input gas stream (hydrogen-containing input gas stream in the context of the invention) is further admixed with steam from conduit 39. This results in conduit 22 in a steam-containing, hydrocarbon-containing and hydrogen-containing input gas stream. This stream is converted into synthesis gas in the autothermal reformer. The autothermal reformer is also supplied with electrolytically produced oxygen as oxidant via conduit 35. The autothermal reformer is moreover supplied via a conduit (not shown) with the still-lacking oxygen for the reaction, in the form of air, oxygen-enriched air or pure oxygen.

Since hydrogen reacts with oxygen in the autothermal reformer only to a small extent, if at all, to afford water, the synthesis gas at the outlet of the autothermal reformer has a high stoichiometry number SN of more than 1.9. Since the autothermal reformer in any case requires oxygen as oxidant it is not necessary to purify the electrolytically produced hydrogen stream in conduit 38 as described for process 2. Since a steam stream is supplied to the hydrogen-containing input gas stream/steam is produced (and reacted) in the course of the partial oxidation in the autothermal reformer 12 it is not necessary to dry the electrolytically produced hydrogen stream either. Inventive process 3 accordingly requires no purification unit 19 as described for FIG. 2.

The synthesis gas stream which has a stoichiometry number of more than 1.9 is sent on via conduit 23 and cooled in the unit for heat recovery 13. The cooled synthesis gas stream is sent on via conduit 40 and may subsequently be directly used for producing methanol in the unit for methanol synthesis 15.

The process shown in FIG. 3 further represents an optimization and alternative to the use of the process water generated in the distillation unit 16. According to the process shown in FIG. 3 the process water is supplied to a water treatment unit 17. According to the quality thereof it may also be directly employed as feed for the electrolyzer, thus bypassing the water treatment unit 17. In this case the process water is directly supplied via conduit 37 to conduit 33 (not shown). In any case the required amount of raw water (conduit 32) and/or pure water (conduit 33) is reduced. Depending on the available amount of process water from distillation unit 16 this may additionally be used for producing steam in the heat recovery unit 13 (not shown in FIG. 3).

Figure 4:
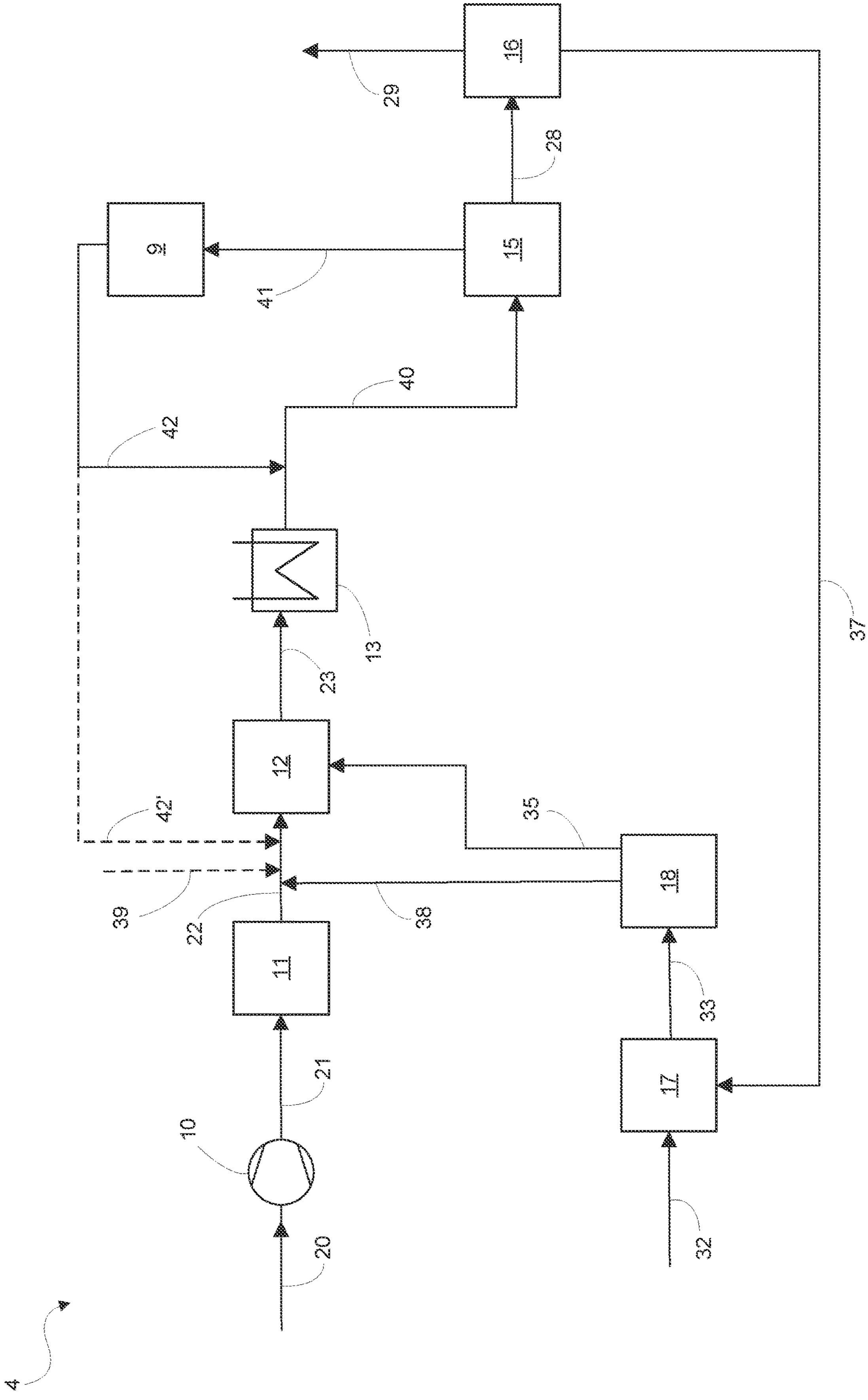

FIG. 4 shows a highly simplified block flow diagram of an example of a further process, here process 4, for synthesis gas production and subsequent methanol production according to the invention.

The process mode according to process 4 shown in FIG. 4 differs from process 3 especially in that a purge gas stream is withdrawn from the methanol synthesis 15 via conduit 41 and sent to an apparatus for pressure swing adsorption (PSA) 9. The purge gas stream is separated from a residual gas stream (not shown) which substantially contains synthesis gas unconverted in the methanol synthesis 9. The apparatus for pressure swing adsorption 9 produces a hydrogen stream and a tail gas stream (tail gas stream not shown). The hydrogen stream, in the context of the invention a non-electrolytically produced hydrogen stream, is sent on via conduit 42 and in conduit 40 combined with the synthesis gas stream produced in the autothermal reformer 12.

Alternatively or in addition the hydrogen stream withdrawn from the PSA 9 could also be supplied to the hydrocarbon-containing input gas stream in conduit 22 in addition to the electrolytically produced hydrogen stream (see dashed conduit 42').

Utilizing the purge gas to produce hydrogen by pressure swing adsorption allows the electrolyzer to be made correspondingly smaller since accordingly said electrolyzer need not produce as much hydrogen for adjusting the stoichiometry number of the synthesis gas stream.

The following numerical examples are based on simulation data and serve to further elucidate the invention. The simulation data were generated using the software AspenPlus®.

The following table shows simulation data for two comparative examples P1 and P2 and two inventive examples P3 and P4, in each case for a process mode with a PDX reactor. P1 in principle corresponds to the process mode of FIG. 1 with production of a hydrogen stream by pressure swing adsorption of reformed synthesis gas. P2 in principle corresponds to the process mode of FIG. 2 with production of a hydrogen stream by electrolysis and supply of the hydrogen stream downstream of the PDX reactor. P3 and P4 in principle correspond to the process mode of FIG. 3 (inventive) with production of a hydrogen stream by electrolysis and supply of the hydrogen stream upstream of the PDX reactor.

Streams are often reported as mole flows in kilomol per hour (kmol/h).

| | P1 (comparative) | P2 (comparative) | P3 (inventive) | P4 (inventive) |
|---|---|---|---|---|
| Natural gas stream (kmol/h) | 404.0 | 316.0 | 316.0 | 316.0 |
| Electrolyzer hydrogen stream (kmol/h) | n/a | 120.0 | 120.0 | 150.0 |
| Oxygen stream (t/h) | 300.0 | 239.0 | 249.9 | 252.7 |
| Synthesis gas stream to PSA | 21.5% | n/a | n/a | n/a |

-continued

| | P1 (comparative) | P2 (comparative) | P3 (inventive) | P4 (inventive) |
|---|---|---|---|---|
| Synthesis gas stream (kmol/h) | 1031.3 | 1032.2 | 1007.7 | 1031.8 |
| Stoichiometry number SN | 1.99 | 1.97 | 1.91 | 1.98 |

The required natural gas stream is markedly higher for P1 since a relatively large proportion of the produced synthesis gas stream (21.5%) needs to be diverted for producing the hydrogen stream by pressure swing adsorption (PSA).

The comparison between P2 and P3 shows that when supplying the same hydrogen stream upwards of the PDX reactor (P3) a slightly lower synthesis gas amount is produced and the resulting synthesis gas exhibits a slightly lower stoichiometry number. Compensating this effect requires increasing the hydrogen stream amount from 120 kmol/hr to 150 kmol/hr (according to P4). The increase in operating costs (OPEX) brought about thereby can be compensated by the corresponding reduction of the capital costs (CAPEX) since according to the invention no purification unit connected downstream of the electrolyzer is required for removal of oxygen. Such a purification unit also increases the operating costs (OPEX) of the corresponding plant.

The following table shows simulation data for two comparative examples A1 and A2 and an inventive example A3, in each case for a process mode with an autothermal reformer (ATR reactor). A1 in principle corresponds to the process mode of FIG. 1 with production of a hydrogen stream by pressure swing adsorption (PSA) of reformed synthesis gas. In addition and not shown in FIG. 1, a further hydrogen stream is produced by a PSA utilizing a purge gas stream generated in the methanol synthesis. This non-electrolytically produced hydrogen stream is supplied to the synthesis gas stream downstream of the autothermal reformer and upstream of the methanol synthesis.

A2 corresponds to the process mode of FIG. 2 with production of a hydrogen stream by electrolysis and supply of this hydrogen stream downstream of the autothermal reformer. In addition and not shown in FIG. 2, a further hydrogen stream is produced by a PSA through utilization of the purge gas stream generated in the methanol synthesis. This non-electrolytically produced hydrogen stream is supplied to the synthesis gas stream downstream of the autothermal reformer and upstream of the methanol synthesis.

A3 corresponds to the process mode according to FIG. 4 (inventive) with production of a hydrogen stream by electrolysis and supply of this hydrogen stream upstream of the autothermal reformer. In addition, a further hydrogen stream is produced by a PSA utilizing the purge gas stream generated in the methanol synthesis. This non-electrolytically produced hydrogen stream is supplied to the synthesis gas stream downstream of the autothermal reformer and upstream of the methanol synthesis.

The examples A1 to A3 also show the synthesis of methanol from the produced synthesis gas in a synthesis loop with a water-cooled reactor at a recycle ratio of 1.6. The recycle ratio (RR) represents the quotient of the stream of recycle gas (residual gas unconverted at the outlet and recycled to the reactor inlet) and freshly supplied synthesis gas.

Streams are often reported as mole flows in kilomol per hour (kmol/h).

| | A1 (comparative) | A2 (comparative) | A3 (inventive) |
|---|---|---|---|
| Natural gas stream (kmol/h) | 7741 | 7394 | 7408 |
| Hydrogen stream from electrolyzer (kmol/h) | n/a | 880 | 1000 |
| Hydrogen stream from PSA (kmol/h) | 1650 | 650 | 700 |
| Oxygen stream (t/h) | 137 | 127 | 128 |
| Synthesis gas stream to PSA (kmol/h) | 1800 | n/a | n/a |
| Synthesis gas stream (kmol/h) | 22 943 | 23 001 | 23 038 |
| Stoichiometry number SN | 2.4 | 2.4 | 2.5 |
| Methanol product (t/d) | 5001 | 5004 | 5001 |

The comparison between A2 and A3 shows that when supplying the hydrogen stream to the natural gas stream upstream of the autothermal reformer a larger hydrogen amount is required to produce the same methanol amount (i.e. synthesis gas amount). The increase in operating costs (OPEX) brought about thereby can be compensated by the corresponding reduction of the capital costs (CAPEX) since according to the invention no purification unit connected downstream of the electrolyzer is required for removal of oxygen. Such a purification unit also increases the operating costs (OPEX) of the corresponding plant.

LIST OF REFERENCE SYMBOLS

1, 2, 3 Process
9 Pressure swing adsorption
10 Compressor
11 Input gas purification
12 Autothermal reformer
13 Heat recovery
14 Pressure swing adsorption
15 Methanol synthesis
16 Distillation
17 Water treatment
18 Electrolyzer
19 Electrolysis hydrogen purification
20 to 42, 42' Conduit It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for producing synthesis gas, comprising:

(a) providing a hydrocarbon-containing input gas stream;

(b) providing an electrolytically produced hydrogen stream;

(c) supplying at least a portion of the electrolytically produced hydrogen stream to the hydrocarbon-containing input gas stream to obtain a hydrogen-containing input gas stream; and (d) reacting the hydrogen-containing input gas stream in the presence of oxygen as oxidant in a reforming step thereby producing a synthesis gas stream.

2. The process according to claim 1, wherein the reforming step comprises an autothermal reforming (ATR) or a partial oxidation (PDX) of the hydrogen-containing input gas stream.

3. The process according to claim 1, wherein an amount of electrolytically produced hydrogen stream supplied to the hydrocarbon-containing input gas stream according to step (c) is adjusted such that a synthesis gas stream having a stoichiometry number SN of 1.9 to 2.5 is obtained according to step (d), wherein $$SN = \frac{n(H_2) - n(CO_2)}{n(CO) + n(CO_2)}, \text{ with } n \text{ in [mol]}.$$

4. The process according to claim 1, wherein the electrolytically produced hydrogen stream contains oxygen as an impurity and the oxygen present as an impurity is not removed before the supplying of the electrolytically produced hydrogen stream to the hydrocarbon-containing input gas stream according to step (c).

5. The process according to claim 1, wherein the electrolytically produced hydrogen stream contains 0.01% to 5% by volume of oxygen as an impurity.

6. The process according claim 1, wherein the process comprises providing an electrolytically produced oxygen stream, wherein the electrolytically produced oxygen stream is used as oxidant in step (d).

7. The process according to claim 1, wherein the process comprises providing an oxygen stream produced by air separation, wherein the oxygen stream produced by air separation is used as oxidant in step (d).

8. The process according to claim 1, wherein a steam stream is supplied to the hydrocarbon-containing input gas stream or the hydrogen-containing input gas stream.

9. The process according to claim 1, wherein the hydrocarbon-containing input gas stream is a natural gas stream or a biogas stream.

10. A process for producing methanol comprising the process for producing synthesis gas according to claim 1, further comprising the step of reacting the synthesis gas stream over a solid methanol synthesis catalyst to afford raw methanol, wherein the raw methanol comprises at least methanol ($CH_3OH$) and water.

11. The process according to claim 10, wherein the raw methanol is separated into pure methanol and water in a thermal separation process.

12. The process according to claim 10, wherein the water separated in the thermal separation process is used as starting material for the electrolytically produced hydrogen.

13. The process according to claim 10, wherein reacting the synthesis gas stream over the solid methanol synthesis catalyst to afford raw methanol generates a residual gas stream containing synthesis gas unconverted into raw methanol, wherein a portion of the residual gas stream is separated as a purge gas stream and wherein the purge gas stream is supplied to a hydrogen recovery apparatus to produce a non-electrolytically produced hydrogen stream and the non-electrolytically produced hydrogen stream is at least partially supplied to the hydrocarbon-containing input gas stream in addition to the electrolytically produced hydrogen stream to obtain the hydrogen-containing input gas stream according to step (c) and/or the non-electrolytically produced hydrogen stream is at least partially supplied to the synthesis gas stream obtained according to step (d).

14. A plant for producing synthesis gas, wherein the plant comprises the following components in fluid connection with one another:

(a) a means configured for providing a hydrocarbon-containing input gas stream;

(b) an electrolyzer configured for providing an electrolytically produced hydrogen stream;

(c) a means configured for supplying at least a portion of the electrolytically produced hydrogen stream to the hydrocarbon-containing input gas stream which make it possible to produce a hydrogen-containing input gas stream;

(d) a reactor configured for reacting the hydrogen-containing input gas stream in the presence of oxygen as oxidant in a reforming step which makes it possible to produce a synthesis gas stream.

15. The plant according to claim 14, wherein the reactor is an autothermal reformer or a reactor configured for a partial oxidation.

16. The plant according to claim 14, wherein the means (c) are configured such that an amount of electrolytically produced hydrogen stream suppliable to the hydrocarbon-containing input gas stream is adjustable such that a synthesis gas stream having a stoichiometry number SN of 1.9 to 2.5 is producible according to (d), wherein $$SN = \frac{n(H_2) - n(CO_2)}{n(CO) + n(CO_2)}, \text{ with } n \text{ in [mol]}.$$

17. The plant according to claim 14, wherein the plant includes no means for removing oxygen occurring as an impurity from the electrolytically producible hydrogen stream.

18. The plant according to claim 14, wherein the electrolyzer is configured for providing an electrolytically produced oxygen stream and the plant comprises means for using the oxygen stream as oxidant in the reactor (d) for reacting the hydrogen-containing input gas stream to afford the synthesis gas stream.

19. The plant according claim 14, wherein the plant comprises an apparatus for air separation, wherein the apparatus for air separation makes it possible to produce an oxygen stream and the plant comprises means for using the oxygen stream as oxidant in the reactor for reacting the hydrogen-containing input gas stream to afford the synthesis gas stream.

20. A methanol plant for producing methanol comprising a plant for producing synthesis gas according claim 14, wherein the methanol plant comprises a methanol synthesis reactor, wherein the methanol synthesis reactor is configured for reacting the synthesis gas producible by the plant to afford raw methanol, wherein the raw methanol contains at least methanol ($CH_3OH$) and water.

* * * * *